(12) United States Patent
Isaka et al.

(10) Patent No.: US 7,105,337 B2
(45) Date of Patent: Sep. 12, 2006

(54) METHOD OF REMOVING EXOGENOUS ENDOCRINE-DISRUPTING CHEMICAL IN WATER

(75) Inventors: Kazuichi Isaka, Chiyoda-ku (JP); Tatsuo Sumino, Chiyoda-ku (JP)

(73) Assignee: Hitachi Plant Engineering & Construction Co., Ltd., Tokyo (JP)

( * ) Notice: Subject to any disclaimer, the term of this patent is extended or adjusted under 35 U.S.C. 154(b) by 25 days.

(21) Appl. No.: 10/050,797

(22) Filed: Jan. 18, 2002

(65) Prior Publication Data

US 2002/0103347 A1  Aug. 1, 2002

(30) Foreign Application Priority Data

Jan. 26, 2001 (JP) ............... 2001-018861

(51) Int. Cl.
*B09B 3/00* (2006.01)
*C12N 11/04* (2006.01)

(52) U.S. Cl. .................... 435/262.5; 435/182
(58) Field of Classification Search ........... 435/177, 435/180; 424/405; 210/601
See application file for complete search history.

(56) References Cited

U.S. PATENT DOCUMENTS

| | | | |
|---|---|---|---|
| 3,860,490 A * | 1/1975 | Guttag | 435/182 |
| 4,576,718 A | 3/1986 | Reischl et al. | 210/616 |
| 4,608,397 A * | 8/1986 | Reischl | 521/101 |
| 5,078,900 A | 1/1992 | Wegner | 210/728 |
| 5,126,309 A | 6/1992 | Chromecek et al. | 502/402 |
| 5,679,364 A * | 10/1997 | Levy | 424/405 |
| 5,928,918 A * | 7/1999 | Offenbacher et al. | 435/182 |
| 6,576,451 B1 * | 6/2003 | Sumino et al. | 435/182 |

FOREIGN PATENT DOCUMENTS

| | | |
|---|---|---|
| EP | 0 398 538 A1 | 11/1990 |
| JP | A-63-65949 | 3/1988 |
| JP | A-12-65881 | 10/1989 |
| JP | A-2001-346575 | 12/2001 |

\* cited by examiner

*Primary Examiner*—David M. Naff
(74) *Attorney, Agent, or Firm*—Oliff & Berridge, PLC

(57) ABSTRACT

Biological treatment for an environmental hormone in water can be efficiently performed by use of a microorganism-immobilized carrier is provided. To biologically remove an environmental hormonal substance in water by a microorganism-immobilized carrier having microorganism immobilized onto a carrier. The microorganism-immobilized carrier is formed of an immobilizing material prepared by mixing and polymerizing a hydrophilic prepolymer and a hydrophobic prepolymer or prepared by polymerizing a prepolymer having a hydrophilic group and a hydrophobic group in a molecule.

5 Claims, 7 Drawing Sheets

HYDROPHILIC PREPOLYMER

HYDROPHOBIC PREPOLYMER

HYDROPHILIC GROUP/HYDROPHOBIC GROUP MIXED PREPOLYMER

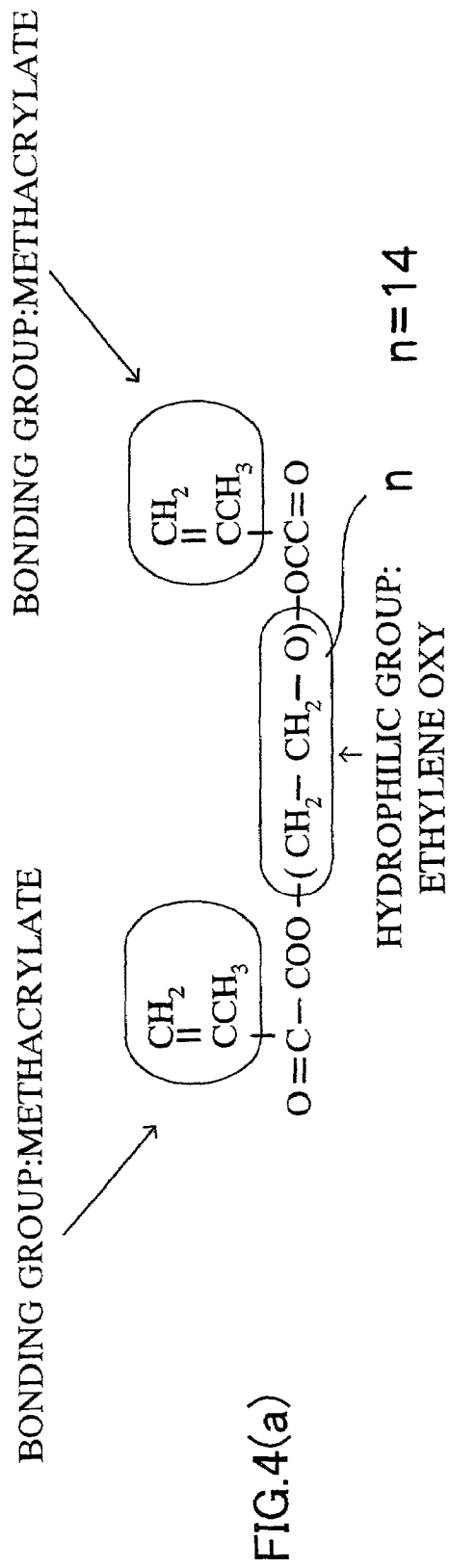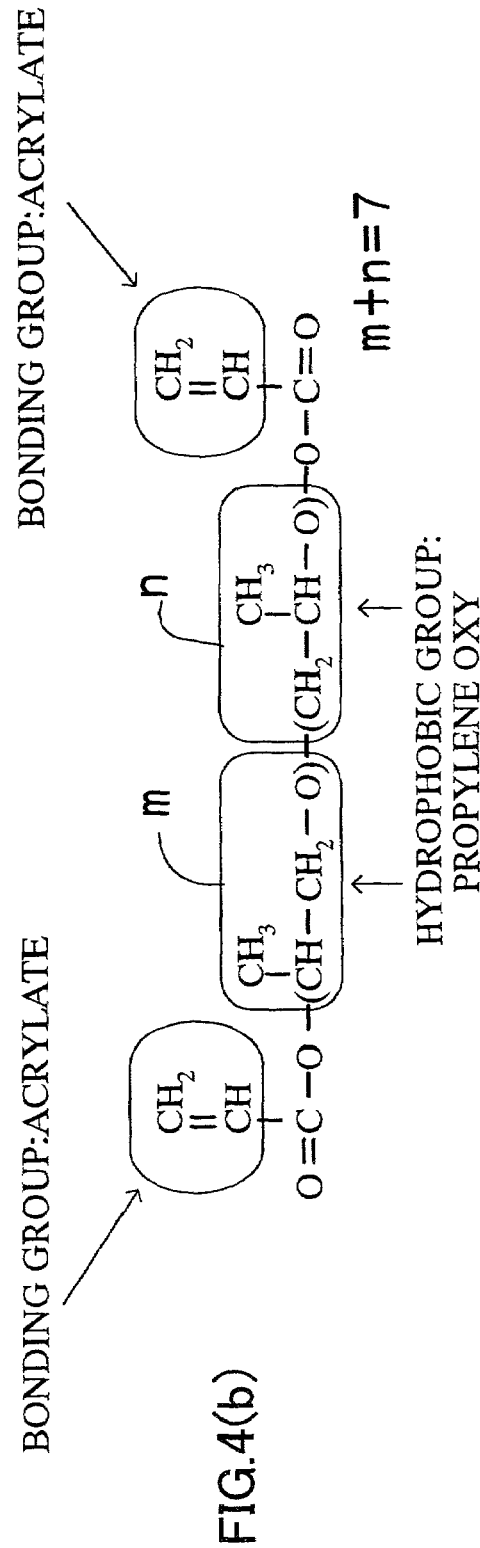
FIG.4(a)
FIG.4(b)

METHOD OF REMOVING EXOGENOUS ENDOCRINE-DISRUPTING CHEMICAL IN WATER

The invention claimed herein is the result of activities undertaken within the scope of a joint research agreement between Hitachi Plant Engineering & Construction Co., Ltd. and Shin-Nakamura Chemical Co., Ltd.

BACKGROUND OF THE INVENTION

1. Field of the Invention

The present invention relates to a method of removing an exogenous endocrine-disrupting chemical (hereinafter referred to as an "environmental hormonal substance") in water, and more particularly, to improvement in the performance of removing the environmental hormonal substance by using a microorganism-immobilized carrier.

2. Description of the Related Art

Chemical substances having in-vivo endocrine-system disrupting activities are present in wastewater such as sewage water and seepage water from landfills. They act as environmental hormonal substances, causing problems. The endocrine systems of living organisms are disrupted by the presence of these environmental hormonal substances, with the result that abnormal reproductions and gender changes from male to female occur, having significant effects upon the ecosystem. The endocrine system of living organisms reacts with extremely sensitivity to such chemicals at certain period of their growth. In humans, the sensitivity is high particularly in fetuses and infants. The effects of the environmental hormonal substances upon them have been a cause of concern. Most environmental hormonal substances are detected at concentrations in the order of several tens μg/L to several ng/L. Although most of environmental hormonal substances are detected in extremely low amounts, they must be disposed of as much as possible in consideration of their effects on the ecosystem as mentioned above.

In the meantime, the environmental hormonal substances present in water can be decomposed to some extent by a biological treatment such as a conventional activated-sludge process. However, the biological treatment has a drawback in that since the environmental hormonal substances are present in extremely low concentrations, they cannot be completely decomposed by microorganisms. To improve the efficiency of the biological treatment, there is a method of maintaining a large amount of microorganism in a reaction vessel by depositing them onto a carrier or immobilized within a carrier. This method is effective in reducing nitrogen or BOD in wastewater, but ineffective in removing the environmental hormonal substances.

SUMMARY OF THE INVENTION

The present invention has been made in view of these problems. An object of the present invention is to provide a method of removing an exogenous endocrine-disrupting chemical in water. This method efficiently removes an environmental hormone in water by a biological process using a microorganism-immobilized carrier.

To attain the aforementioned object, the present invention is directed to a method of biologically removing an exogenous endocrine-disrupting chemical in water by use of a microorganism-immobilized carrier having microorganism immobilized onto a carrier. In this method, the carrier is formed of an immobilizing material which is prepared by mixing and polymerizing a hydrophilic prepolymer and a hydrophobic prepolymer or formed of an immobilizing material prepared by polymerizing a prepolymer having a hydrophilic group and a hydrophobic group mixed in its molecule.

According to the present invention, the carrier on which microorganism to be immobilized is formed of an immobilizing material prepared by mixing and polymerizing a hydrophilic prepolymer and a hydrophobic prepolymer or prepared by polymerizing a prepolymer having a hydrophilic group and a hydrophobic group mixed in its molecule. Therefore, the properties of adsorbing an environmental hormonal substance by the microorganism-immobilized carrier can be enhanced without degrading the affinity with the microorganism. By virtue of this, the contact efficiency between the microorganism immobilized on the microorganism-immobilizing carrier in a high concentration and an environmental hormonal substance can be drastically improved. As a result, the performance of biologically removing the environmental hormonal substance by the microorganism can be improved.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIGS. 4(a) and 4(b) are diagrams showing chemical structures of a hydrophilic prepolymer and a hydrophobic prepolymer;

DETAILED DESCRIPTION OF THE PREFERRED EMBODIMENTS

Preferred embodiments of the method of removing an exogenous endocrine-disrupting chemical in water according to the present invention will be explained with reference to the accompanying drawings.

The present invention enhances the biological removal of an environmental hormonal substance in water by using a microorganism-immobilized carrier (having microorganism immobilized thereon) capable of improving the adsorption of the environmental hormonal substance without decreasing the affinity with the microorganism. To explain more specifically, most of environmental hormonal substances have hydrophobic characteristics, so that they have natures likely to adsorb a hydrophobic material. Therefore, to improve the adsorption efficiency, the hydrophobic material may be used. However, if a carrier is formed of the hydrophobic material alone, the carrier becomes rarely dissolved in water, lowering the affinity to microorganism.

Accordingly, the present inventors have conducted extensive studies on immobilizing materials for forming the carrier which can improve the adsorption to an environmental hormonal substance without degrading the affinity with microorganism. As a result, they found two types of immobilizing materials. One is a prepolymer mixture type immobilizing material having a hydrophilic prepolymer and a hydrophobic prepolymer mixed therein. The other is a hydrophilic group/hydrophobic group mixture type immobilizing material having a hydrophilic group and a hydrophobic group mixed in a molecule of a prepolymer.

First, the prepolymer-mixture type immobilizing material will be explained.

Figure 1:
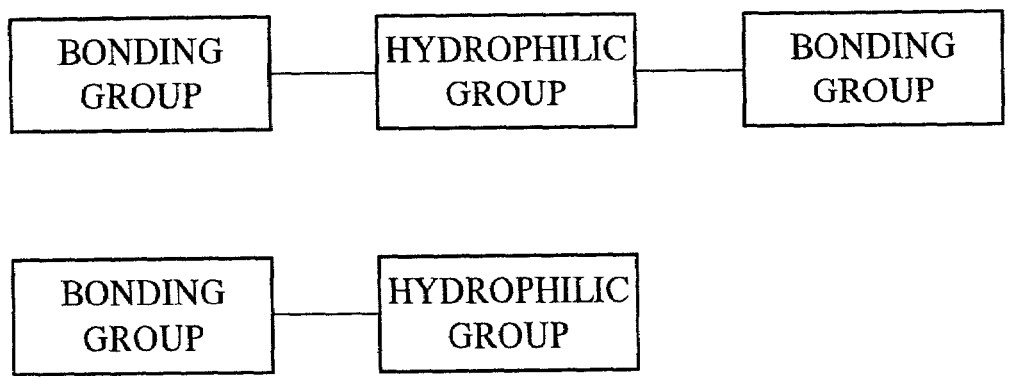
FIG. 1 is a diagram showing a structure of a hydrophilic prepolymer.

The basic skeleton of the hydrophilic prepolymer is as shown in FIG. 1. The prepolymer has at least one bonding group at the ends. To the bonding group, a hydrophilic group is bound. The bonding group binds to a prepolymer in the periphery thereof by a polymerization reaction to form a carrier. Specific examples of the bonding group include monoacrylates, monomethacrylates, diacrylates, dimethacrylates, monourethaneacrylates, diurethaneacrylates and prepolymers having a light-curing polymerization group. However, the bonding group is not particularly limited as long as it can polymerize by a radical reaction. As the hydrophilic group, there are ethyleneoxy, vinyl alcohol, and the like.

Figure 2:
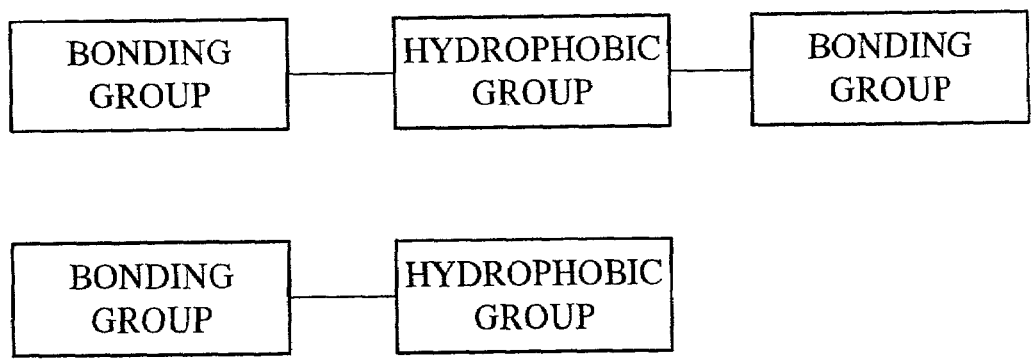
FIG. 2 is a diagram showing a structure of a hydrophobic prepolymer.

On the other hand, the basic skeleton of the hydrophobic prepolymer is as shown in FIG. 2. The prepolymer has at least one bonding group at the ends. To the bonding group, a hydrophobic group is bound. The bonding group binds to a prepolymer in the periphery thereof by a polymerization reaction to form a carrier. Specific examples of the bonding group include monoacrylates, monomethacrylates, diacrylates, dimethacrylates, monourethaneacrylates, diurethaneacrylates and prepolymers having a light-curing polymerization group. However, the bonding group is not particularly limited as long as it can polymerize by a radical reaction. As the hydrophobic group, there are an alkyl group, propyleneoxy, buthyleneoxy and the like.

The hydrophilic prepolymer is preferably mixed with the hydrophobic prepolymer in such a manner that the hydrophobic prepolymer is contained in a ratio of 1% to 40% of the total weight of the hydrophilic prepolymer and the hydrophobic prepolymer. If the mixing ratio of the hydrophobic prepolymer is less than 1% by weight, the adsorption of an environmental hormonal substance are not apparently improved. On the other hand, if the hydrophobic prepolymer is contained in excess of 40%, the hydrophobic group is rarely mixed with the hydrophilic group, affecting the performance of immobilizing microorganism. As a result, the carrier fails to hold a large amount of microorganisms.

To manufacture the microorganism-immobilizing carrier by using the prepolymer-mixture type immobilizing material, the prepolymer is mixed with microorganism and polymerized, thereby immobilizing the microorganism within the carrier (an inclusion immobilization type microorganism-immobilized carrier). Alternatively, the microorganism-immobilizing carrier may be formed by polymerizing the prepolymer molecules to form a carrier without introducing microorganism into the carrier, and then, attaching the microorganism to the surface of the carrier (an attach-immobilization type microorganism-immobilized carrier).

Now, the hydrophilic group/hydrophobic group mixture type immobilizing material will be explained.

Figure 3A:
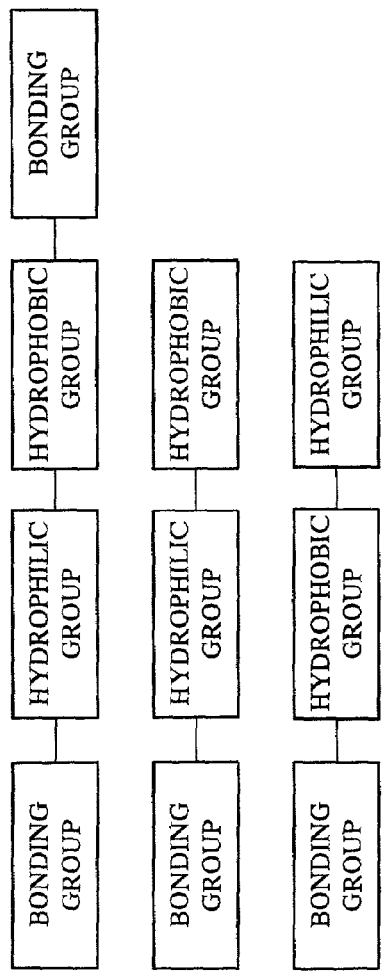
FIGS. 3(a) and 3(b) are diagrams showing structures of hydrophilic group/hydrophobic group mixed prepolymers.
Figure 3B:
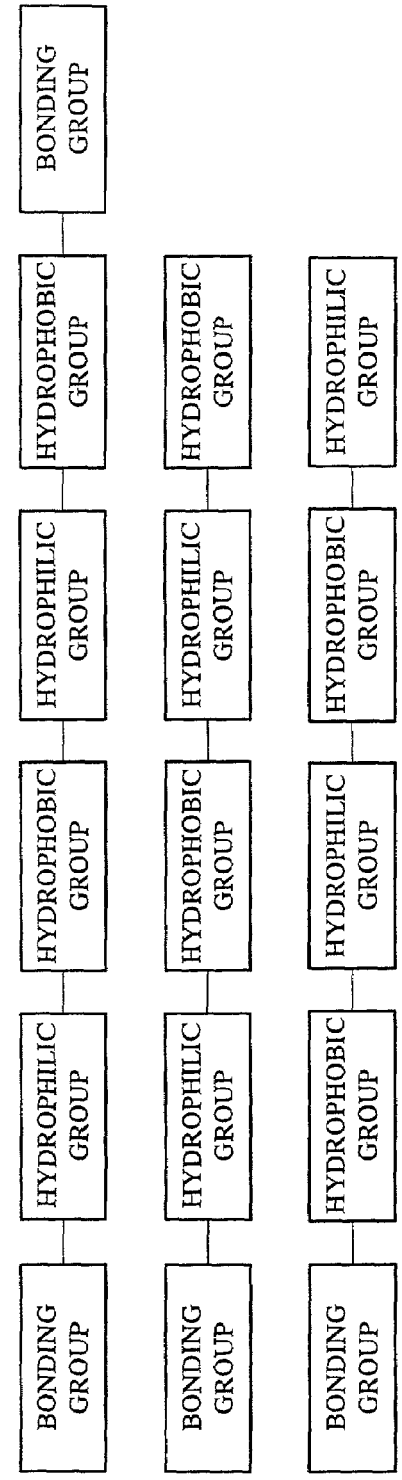

FIGS. 3(a) and 3(b) show basic skeletons of prepolymers having a hydrophilic group and a hydrophobic group mixed therein. Each of the prepolymers has at least one bonding group at the ends. To the bonding group, a main chain consisting of a hydrophilic group and a hydrophobic group is bonded. The bonding group binds to a prepolymer around the bonding group by a polymerization reaction to form a carrier. Specific examples of the bonding group include monoacrylates, monomethacrylates, diacrylates, dimethacrylates, monourethaneacrylates diurethaneacrylates and prepolymers having a light-curing polymerization group. However, the bonding group is not particularly limited as long as it has a bonding group capable of polymerizing by a radical reaction. As the hydrophilic group, there are ethyleneoxy, vinyl alcohol, and the like. As the hydrophobic group, there are alkyl group, propyleneoxy, butyleneoxy and the like.

The main chain consists of a hydrophilic group and a hydrophilic group. The binding order of them is not limited. However, it is preferable that they bind alternately as shown in FIG. 3(b). At this time, the ratio of the hydrophilic group to the hydrophobic group preferably ranges from 99:1 to 30:70. This is because if the ratio of the hydrophobic group to the sum of the hydrophilic group and hydrophobic group is less than 1% (if the ratio of the hydrophilic group to the hydrophobic group is 99:1, the ratio of the hydrophobic group is lower than this ratio), the effect of adsorbing an environmental hormonal substance is not rarely produced. On the other hand, in the case where the ratio of the hydrophobic group to the sum of the hydrophilic group and the hydrophobic group exceeds 70% (if the ratio of the hydrophilic group to the hydrophobic group is 30:70, the ratio of the hydrophobic group is higher than this), the prepolymer is rarely dissolved in water. Since the prepolymer cannot sufficiently mix with microorganism(s), a carrier having a large amount of the microorganism immobilized therein cannot be obtained.

To manufacture the microorganism-immobilizing carrier by use of the hydrophilic group/hydrophobic group mixture type immobilizing material, the prepolymer is mixed with microorganism and then polymerized. As a result, the microorganism is immobilized within the carrier (an inclusion immobilization type microorganism-immobilized carrier). Alternatively, the microorganism-immobilized carrier may be formed by polymerizing the prepolymer to form a carrier without introducing microorganism into the carrier and then attaching the microorganism to the surface of the carrier (an attach-immobilization type microorganism-immobilized carrier).

To remove an environmental hormonal substance in water by using the microorganism-immobilized carrier formed of the prepolymer mixture type or the hydrophilic group/hydrophobic group mixture type immobilizing material, the microorganism-immobilized carrier is loaded into a reaction vessel, water containing an environmental hormonal substance is allowed to flow in, thereby bringing the environmental hormonal substance in water into contact with the microorganism-immobilized carrier.

As mentioned above, in order to biologically remove an environmental hormonal substance in water, the present invention employs a microorganism-immobilized carrier having microorganism immobilized thereon, which is formed of an immobilizing material prepared by mixing and polymerizing a hydrophilic prepolymer and a hydrophobic prepolymer or an immobilizing material prepared by polymerizing the prepolymer having a hydrophilic group and a hydrophobic group mixed in its molecule.

As a result, a large amount of the microorganism is carried by the microorganism-immobilizing carrier. In addition, a large amount of an environmental hormonal substance can be collected and concentrated around the microorganism held in a large concentration. Therefore, the contact efficiency between the microorganism and the environmental hormonal substance can be increased, improving a decomposition efficiency of the environmental hormonal substance by the microorganism. As a result, the environmental hormonal substance present in water at an extremely small concentration in the order of several tens μg/L to several ng/L can be efficiently treated by a biological process. Thus, the performance of removing the environmental hormonal substance can be tremendously improved. In this case, if a conventional immobilization material, such as polyethyleneglycol-based materials, polyacrylamide-based materials, polyvinyl alcohol, agar, and sodium alginate, exhibiting only hydrophilic properties, is used, microorganism can be carried at a high concentration. However, the adsorption amount of the environmental hormonal substance cannot be increased. Hence, the performance of removing the environmental hormonal substance cannot be improved.

Types of water to be subjected to the present invention include, but not particularly limited to, sewage water, seepage water from landfills, industrial wastewater, and river water. An environmental hormonal substance is known to be easily taken up into sludge. It is also known that when extra sludge discharged from water treatment process is dewatered, the discharged water contains a large amount of an environmental hormonal substance. It is thus useful that the present invention is applied to the discharged water.

As the environmental hormonal substances to be subjected by the present invention, the Japanese Environment Agency has pointed out 67 substance groups. The environment health division of the Japanese Environment Agency has investigated current conditions of them. Specific examples of the environmental hormonal substances include dioxins, polychlorinated biphenyls (PCB), polybrominated biphenyls (PBB), hexachlorobenzenes (HCB), pentachlorophenol (PCP), 2,4,5-tri phenoxyacetic acid, 2,4-dichlorophenoxyacetic acid, amitrole, atrazine, arachlor, simazine (CAT), hexachlorocyclohexane (HCH), ethylparathion, carbaryl(NAC), chlordane, oxychlordane, trans-nonachlor, 1,2-dibromo-2-chloropropane, DDT, DDE, DDD, quercetin, Aldrin, endrin, dildrin, endosulfan(benzoepin), heptachlor, heptachlorepoxide, malathion, mesomil, methoxychlor, mirex, nitrophene, toxaphene, tributyltin, triphenyltin, trifluralin, 4-n-pentylphenol, 4-n-hexylphenol, 4-n-heptylphenol, octyl phenol, nonylphenol, bisphenol A, di-2-ethylhexyl phthalate, butyl benzyl phthalate, di-n-butyl phthalate, dicyclohexyl phthalate, diethyl phthalate, benzo(a) pyrene, 2,4-dichlorophenol, adipic acid di(2-ethylhexyl)ester, benzophenone, 4-nitrotoluene, octachlorostyrene, aldicarb, benomyl, kepone, mancozeb, metiram, metribuzin, cypermethrin, esvanvalate, vanvalate, permethrin, vinclozolin, zineb, ziram, dipentyl phthalate, dihexyl phthalate, dipropyl phthalate, styrene dimer, styrene trimer, and n-butyl benzene. However, substances other than the aforementioned substances may have endocrine-disrupting activities. The EPA (Environmental Protection Agency) of the United State has enlarged the number of target substances to 15,000 types and checked as to whether they act as environmental hormonal substances. Hence, the endocrine-disrupting substances are not limited to the substances mentioned above. Most of these materials are characterized by having hydrophobic properties (difficult to be dissolved in water).

EXAMPLES

Example 1

Prepolymer-Mixture Type Immobilizing Material

As shown in FIGS. 4(a) and 4(b), polyethyleneglycol dimethacrylate was used as a hydrophilic prepolymer and polypropyleneglycol diacrylate was used as a hydrophobic prepolymer. The polyethyleneglycol dimethacrylate used as the hydrophilic prepolymer had ethyleneoxy as a hydrophilic group and methacrylate as a bonding group, which was arranged at both ends. The polypropyleneglycol diacrylate serving as the hydrophobic prepolymer had a propyleneoxy as a hydrophobic group and acrylate as a bonding group, which was arranged at both ends. The test carriers had four types of mixing ratios of hydrophobic prepolymers, which were set at 0%, 5%, 10% and 20% by weight. Note that the hydrophilic prepolymer was sufficiently mixed with and dissolved in water, whereas the hydrophobic prepolymer was not dissolved in water. Thus, microorganism was mixed with a gel while stirring, and polymerized by a radical reaction to immobilize a large amount (high concentration) of microorganism(s) within the carrier having the hydrophilic group and the hydrophobic group. The inclusive immobilization type microorganism-immobilized carrier was formed in this manner.

Figure 5:
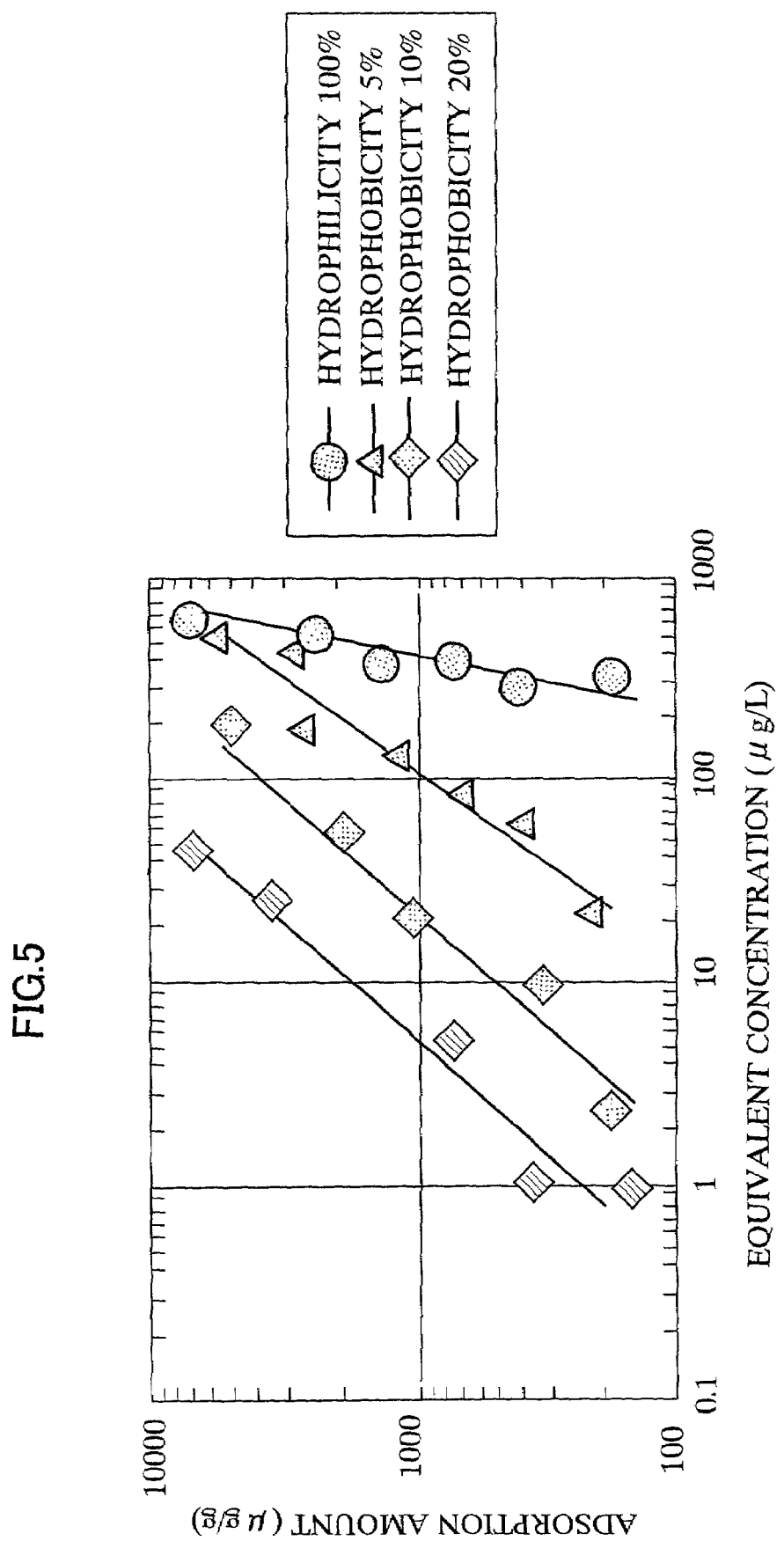
FIG. 5 is a graph showing environmental hormonal substance adsorption characteristics of the microorganism-immobilized carrier formed of an immobilizing material of a prepolymer mixture type.
Figure 6:
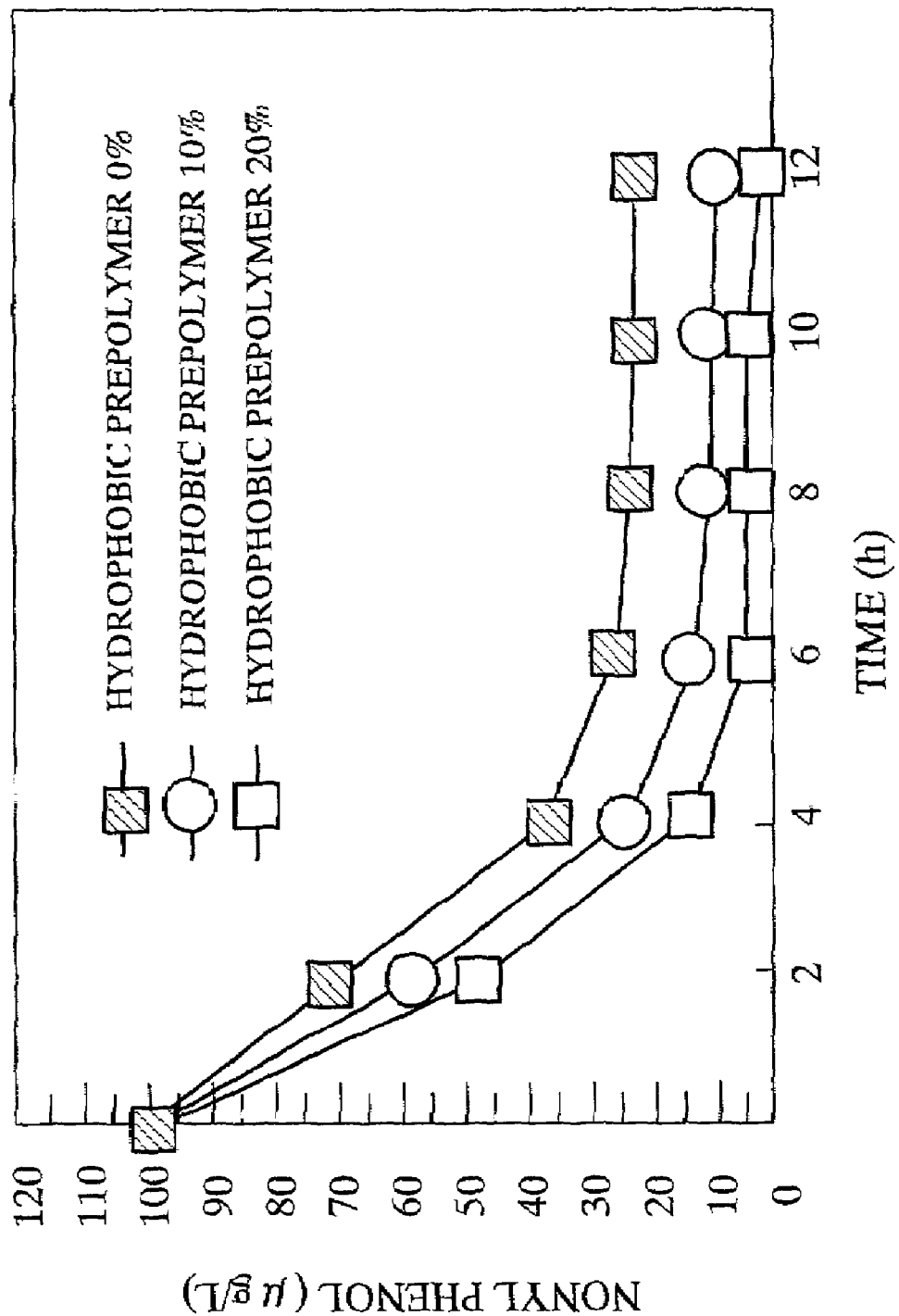
FIG. 6 is a graph showing the performance of removing an environmental hormonal substance by the microorganism-immobilized carrier formed of an immobilizing material of a prepolymer mixture type.

The adsorption properties of the microorganism-immobilized carrier formed of the prepolymer-mixture type immobilizing material as mentioned above were checked. The results are shown in FIG. 5. FIG. 6 shows the results on the treatment performance of environmental hormonal substances.

In the first place, the adsorption of an environmental hormonal substance, nonyl phenol, was checked by the microorganism-immobilized carrier. As a result, adsorption isotherms shown in FIG. 5 were obtained. In FIG. 5, the steeper the slopes of the adsorption isotherms, the lower the adsorption performances. The adsorption properties degrade as the adsorption isotherms go to the right-hand side. The results demonstrate that as the content of the hydrophobic prepolymer in the microorganism-immobilized carrier increases, the adsorption isotherm moves to the upper left-hand side. It is therefore apparent that the adsorption of the environmental hormonal substance by the microorganism-immobilized carrier is improved.

Furthermore, the performance of treating nonyl phenol by use of the microorganism-immobilized carrier was checked. The experiment was performed by pouring 1 L of ultra pure water in a 3 L reaction vessel (Erlenmeyer flask) and adding 100 μg/L of nonyl phenol. The packing ratio of the microorganism-immobilized carrier was set at 10% by volume of the reaction vessel. As a result, in the case of a microorganism-immobilized carrier formed of a prepolymer mixture containing no hydrophobic prepolymer, the amount of nonyl phenol decreased to about 30 μg/L, as shown in FIG. 6. In contrast, in the case of a microorganism-immobilized carrier formed of a prepolymer mixture containing 10% of a hydrophobic prepolymer, the amount of nonyl phenol decreased to about 10 μg/L. In the case of a microorganism-immobilized carrier formed of a prepolymer mixture containing 20% of a hydrophobic prepolymer, the amount of nonyl phenol decreased to about 5 μg/L. From the above, it is apparent that nonyl phenol can be treated to a lower concentration for shorter time by mixing a hydrophobic prepolymer into a hydrophilic prepolymer. When the amount of nonyl phenol remaining in the microorganism-immobilized carrier was measured after the treatment was completed, only one part by weight of the decrease amount of nonyl phenol was left within the carrier. It is therefore confirmed that nonyl phenol was decomposed by the microorganism present in the carrier. Incidentally, when the mixing ratio of a hydrophobic prepolymer by weight exceeded 40%, the adsorption performance of the microorganism-immobilized carrier to nonyl phenol increased. However, the hydrophilic property of the carrier extremely deteriorated, with the result that the carrier failed to hold a large amount of microorganisms. As a result, the treatment performance cannot be improved.

Example 2

Hydrophilic Group/Hydrophobic Group Mixture Type Immobilizing Material

Figure 7:
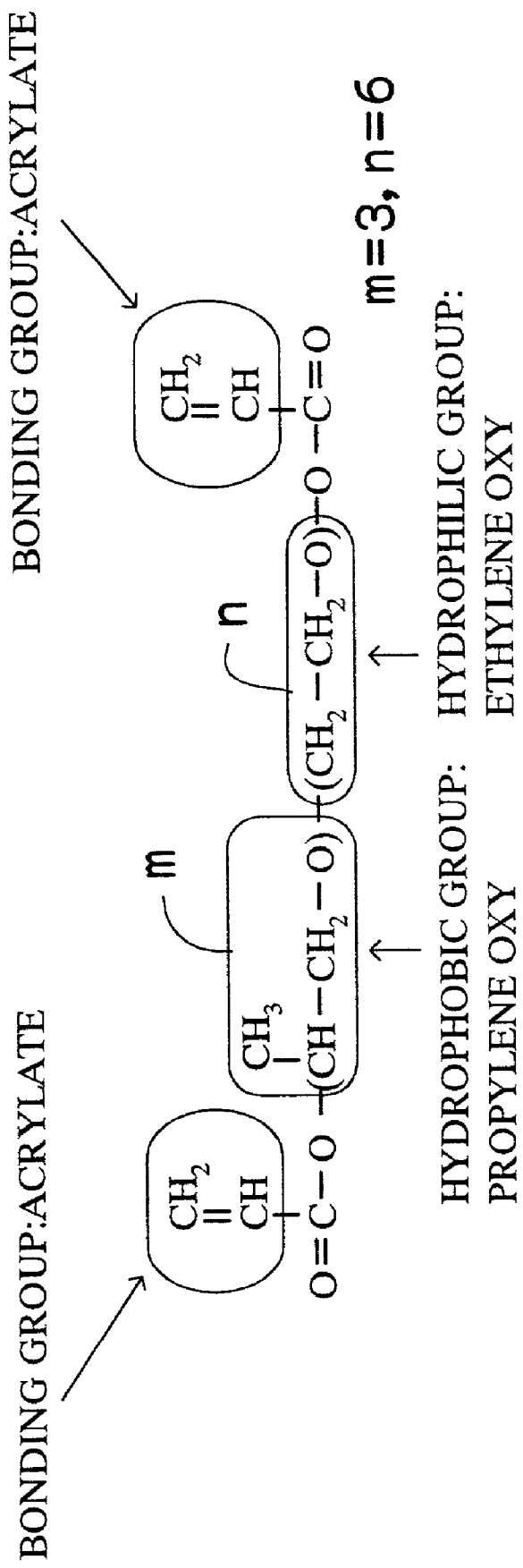
FIG. 7 shows chemical structure of a prepolymer having a hydrophilic group and a hydrophobic group in a molecule.

As shown in FIG. 7, a prepolymer contains a hydrophilic group and a hydrophobic group in a molecule. As the hydrophilic group, ethyleneoxy (n=6) was used. As the hydrophobic group, propyleneoxy (m=3) was used. More specifically, the ratio of the hydrophilic group to the hydrophobic group was 6:3. The main chain is formed of ethyleneoxy and propyleneoxy. To the ends of the main chain, an acrylate group serving as a bonding group was added. The prepolymer and microorganism was mixed and polymerized to form an inclusion-immobilized type microorganism-immobilized carrier having a large amount of the microorganism.

Figure 8:
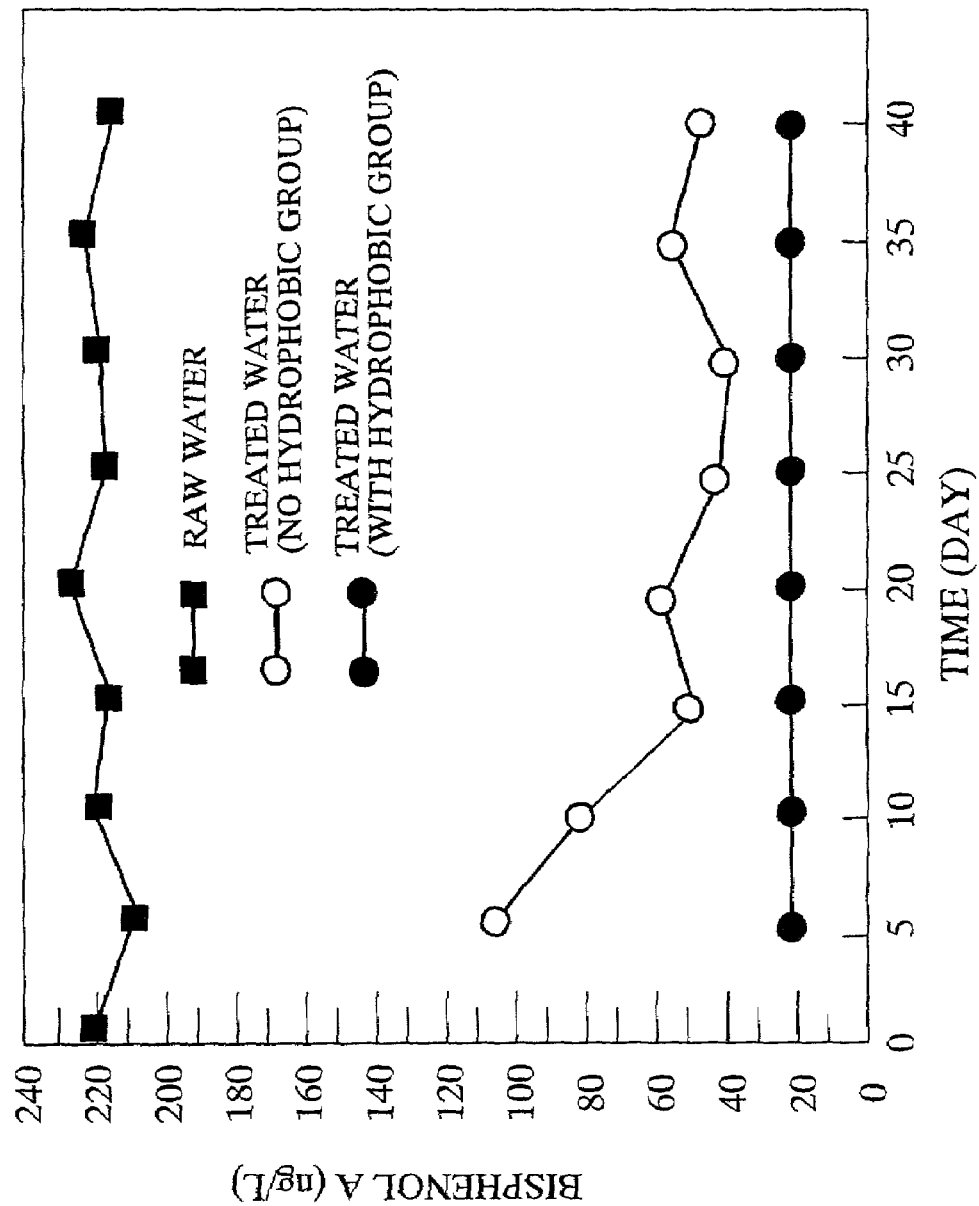
FIG. 8 is a graph for explaining the performance of removing an environmental hormonal substance by the microorganism-immobilized carrier formed of an immobilizing material of a hydrophilic group/hydrophobic group mixture type.

FIG. 8 shows the performance of treating bisphenol A of sewage water (concentration in raw water was about 220 ng/L) by the microorganism-immobilized carrier having a hydrophobic group and two types of microorganism-immobilized carriers containing no hydrophobic group, all formed in accordance with the aforementioned method. Experiment was performed by using an airlift type reactor (an effective volume of 1 L) formed of glass. Treatment was continuously performed by setting the retention time at 6 hours. The packing ratio of the microorganism-immobilized carrier was set at 10% by volume.

The results are shown in FIG. 8. The content of bisphenol A in water decreased at last to about 50 ng/L after the treatment was performed for 15 hours by the microorganism-immobilized carrier having no hydrophobic group. The concentration of bisphenol A subsequently remains at the same level as about 50 ng/L. In contrast, the content of bisphenol A in the water decreased to about 20 ng/L after the treatment was performed for 5 hours by the microorganism-immobilized carrier containing a hydrophobic group. The concentration of bisphenol A subsequently remains at the same level as about 20 ng/L.

FIG. 4(b) shows a prepolymer (n=14, m+n=7). However, even if a prepolymer (n=2–20, m+n=2–26) is used, the same tendency is shown with respect to the performance of removing bisphenol A. In the experiment of FIG. 7, a prepolymer (n=6, m=3) was used. However, even if a prepolymer (n=1–20, m=1–20) was used, the same tendency was shown with respect to the performance of removing bisphenol A.

As explained in the foregoing, according to a method of removing an exogenous endocrine-disrupting chemical in water of the present invention, biological treatment of environmental hormones in water can be efficiently performed by use of the microorgamsm-immobilized carrier.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A method of producing a microorganism-immobilized carrier for removing an exogenous endocrine-disrupting chemical in water, the method comprising:
    mixing microorganisms, a hydrophilic prepolymer having a hydrophilic group, and a hydrophobic prepolymer having a hydrophobic group, wherein a mixing ratio of the hydrophobic prepolymer to the total weight of the hydrophilic prepolymer and the hydrophobic prepolymer falls within a range of 1% to 40%; and
    polymerizing the hydrophilic prepolymer and the hydrophobic prepolymer to form the microorganism-immobilized carrier within which the microorganisms are inclusively immobilized, the microorganism-immobilized carrier being provided with the hydrophilic group and the hydrophobic group, the microorganisms decomposing the exogenous endocrine-disrupting chemical.

2. A microorganism-immobilized carrier produced by the method according to claim 1.

3. A method of removing an exogenous endocrine-disrupting chemical in water, the method comprising:
    loading the microorganism-immobilized carrier according to claim 2 into a reaction vessel; and
    flowing the water containing the exogenous endocrine-disrupting chemical into the reaction vessel, thereby bringing the exogenous endocrine-disrupting chemical into contact with the microorganism-immobilized carrier and decomposing the exogenous endocrine-disrupting chemical.

4. A method of removing an exogenous endocrine-disrupting chemical in water, the method comprising bringing the water into contact with the microorganism-immobilized carrier of claim 2, wherein exogenous endocrine-disrupting chemical in said water is decomposed by microorganisms in said microorganism-immobilized carrier.

5. The method according to claim 1, wherein said hydrophilic prepolymer comprises ethyleneoxy and said hydrophobic prepolymer comprises propyleneoxy.

* * * * *